US009623159B2

(12) United States Patent
Locke

(10) Patent No.: US 9,623,159 B2
(45) Date of Patent: Apr. 18, 2017

(54) INTERFACES, SYSTEMS, AND METHODS FOR USE IN REDUCED PRESSURE TISSUE TREATMENT

(71) Applicant: KCI Licensing, Inc., San Antonio, TX (US)

(72) Inventor: Christopher Brian Locke, Bournemouth (GB)

(73) Assignee: KCI Licensing, Inc., San Antonio, TX (US)

( * ) Notice: Subject to any disclaimer, the term of this patent is extended or adjusted under 35 U.S.C. 154(b) by 836 days.

(21) Appl. No.: 13/955,662

(22) Filed: Jul. 31, 2013

(65) Prior Publication Data

US 2014/0039424 A1    Feb. 6, 2014

Related U.S. Application Data

(60) Provisional application No. 61/679,282, filed on Aug. 3, 2012.

(51) Int. Cl.
*A61M 1/00* (2006.01)
*A61M 27/00* (2006.01)

(52) U.S. Cl.
CPC ........ *A61M 1/0088* (2013.01); *A61M 1/0076* (2013.01); *A61M 1/0086* (2014.02); *A61M 1/0092* (2014.02); *A61M 1/0058* (2013.01); *A61M 27/00* (2013.01); *A61M 2205/3344* (2013.01)

(58) Field of Classification Search
CPC .............. A61M 1/0088; A61M 1/0086; A61M 1/0092; A61M 1/0076; A61M 2205/3344

USPC ......................................................... 604/319
See application file for complete search history.

(56) References Cited

U.S. PATENT DOCUMENTS

| 1,355,846 | A | 10/1920 | Rannells |
| 2,547,758 | A | 4/1951 | Keeling |
| 2,632,443 | A | 3/1953 | Lesher |

(Continued)

FOREIGN PATENT DOCUMENTS

| AU | 550575 A1 | 3/1986 |
| AU | 745271 | 4/1999 |

(Continued)

OTHER PUBLICATIONS

International Search Report and Written Opinion for corresponding PCT/US2013/053002 mailed Dec. 5, 2013.

(Continued)

*Primary Examiner* — Philip R Wiest
*Assistant Examiner* — Andrew J Mensh

(57) ABSTRACT

Systems and devices for treating a tissue site may include an interface adapted to provide a reduced pressure to a dressing. The interface may include a positive-pressure channel for delivering a positive pressure from a positive-pressure port to a positive pressure outlet. The positive-pressure channel may include a constricted portion configured to provide a pressure drop. The interface may additionally include a reduced-pressure channel adapted to deliver reduced pressure to the dressing that substantially corresponds to the pressure drop. The reduced-pressure channel may be fluidly coupled between the positive pressure channel and a side of the interface body adapted to face the dressing. Other systems and devices are disclosed.

24 Claims, 5 Drawing Sheets

(56) References Cited

U.S. PATENT DOCUMENTS

| | | |
|---|---|---|
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielson |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2007/0167926 A1* | 7/2007 | Blott .................. A61M 1/0084 604/304 |
| 2010/0016767 A1 | 1/2010 | Jones et al. |
| 2010/0063483 A1* | 3/2010 | Adahan ............... A61M 1/0088 604/543 |
| 2010/0305523 A1* | 12/2010 | Vess .................... A61M 1/0001 604/313 |
| 2011/0015565 A1* | 1/2011 | Hursey ............... A61F 13/0203 604/24 |
| 2012/0143114 A1* | 6/2012 | Locke ............... A61F 13/00068 602/43 |
| 2013/0317406 A1* | 11/2013 | Locke ............... A61F 13/00051 602/46 |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| JP | 4129536 | 4/1992 |
| SG | 71559 | 4/2002 |
| WO | 80/02182 | 10/1980 |
| WO | 87/04626 | 8/1987 |
| WO | 90/10424 | 9/1990 |
| WO | 93/09727 | 5/1993 |
| WO | 94/20041 | 9/1994 |
| WO | 96/05873 | 2/1996 |
| WO | 97/18007 | 5/1997 |
| WO | 99/13793 | 3/1999 |
| WO | 00/38755 A2 | 7/2000 |
| WO | 2009/081181 A1 | 7/2009 |

OTHER PUBLICATIONS

N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University,

(56) References Cited

OTHER PUBLICATIONS

Cheboksary, U.S.S.R. 1986);pp. 94-96 (certified translation).
Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.
Susan Mendez-Eastmen, RN; "When Wounds Won't Heal" RN Jan. 1998, vol. 61 (1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), vol. 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, p. 1.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., vol. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovic, V. Ð ukić, Ž. Maksimović, Ð . Radak, and P. Peška, "Vacuum Therapy in the Treatment of Peripheral Blood Vessels," Timok Medical Journal 11 (1986), pp. 161-164 (certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, "An Improved Sump Drain-Irrigation Device of Simple Construction," Archives of Surgery 105 (1972) pp. 511-513.
C.E. Tennant, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians (Jul. 2007).

* cited by examiner

INTERFACES, SYSTEMS, AND METHODS FOR USE IN REDUCED PRESSURE TISSUE TREATMENT

RELATED APPLICATION

This application claims the benefit, under 35 USC §119 (e), of the filing of U.S. Provisional Patent Application Ser. No. 61/679,282, entitled "INTERFACES, SYSTEMS, AND METHODS FOR USE IN REDUCED PRESSURE TISSUE TREATMENT," filed 3 Aug. 2012, which is incorporated herein by reference for all purposes.

BACKGROUND

The present disclosure relates generally to medical treatment systems, and more particularly, but not by way of limitation, to interfaces, systems, and methods for use in reduced pressure tissue treatment.

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, which may include faster healing and increased formulation of granulation tissue.

SUMMARY

According to an illustrative embodiment, a positive-pressure wound interface for providing reduced pressure to a reduced-pressure dressing on a tissue site is presented. The positive-pressure wound interface includes an interface body having a first side and a second, tissue-facing side. An inlet is formed in the interface body that includes a positive-pressure port and a reduced-pressure-sensing port. The positive-pressure port is fluidly isolated from the reduced-pressure-sensing port proximate the inlet. The positive-pressure wound interface further includes a positive-pressure channel extending though the interface body from the positive-pressure port to a positive-pressure outlet. The positive-pressure channel is configured to deliver a positive pressure through the interface body from the positive-pressure port downstream to the positive pressure outlet. The positive-pressure channel includes at least one constricted portion. The positive-pressure wound interface further includes a reduced-pressure channel. The reduced-pressure channel includes a first end and a second, tissue-facing end, such that the first end of the reduced-pressure channel is fluidly coupled to the positive-pressure channel and the second, tissue-facing end is fluidly coupled to a tissue inlet that is proximate a tissue-facing side of the interface body. The reduced-pressure channel extends from the positive-pressure channel to the tissue-facing side of the interface body and is configured to deliver reduced pressure to the tissue site. The positive-pressure channel is configured to produce the reduced pressure by a Venturi effect as positive pressure flows through the positive-pressure channel and past the reduced-pressure channel. The positive-pressure wound interface also includes a reduced-pressure-sensing channel that extends from the reduced-pressure-sensing port to the tissue-facing side of the interface body.

In another illustrative embodiment, a system for treating a tissue site on a patient with reduced pressure includes a manifold for placing proximate the tissue site. The manifold has a first side and a second, tissue-facing side and comprises an absorbent layer for absorbing liquids from the tissue site. The system further includes a flexible film drape that has a first side and a second, tissue-facing side for covering the first side of the manifold to form a sealed space containing the manifold. The flexible film drape has an aperture formed proximate the first side of the manifold. The system includes a positive-pressure wound interface having a first side and a second, tissue-facing side for positioning over the flexible film drape. The second, tissue-facing side of the interface is disposed on the flexible film drape proximate the aperture. The positive-pressure wound interface includes an interface body having a first side and a second, tissue-facing side, and an inlet formed in the interface body. The inlet has a positive-pressure port and a reduced-pressure-sensing port, such that the positive-pressure port is fluidly isolated from the reduced-pressure-sensing port proximate the inlet. The interface further includes a positive-pressure channel that extends though the interface body from the positive-pressure port to a positive-pressure outlet. The positive-pressure channel is configured to deliver a positive pressure through the interface body from the positive-pressure port downstream to the positive-pressure outlet. The positive-pressure channel includes at least one constricted portion. The positive-pressure wound interface further includes a reduced-pressure channel having a first end and a second, tissue-facing end, such that the first end of the reduced-pressure channel is fluidly coupled to the positive-pressure channel and the second, tissue-facing end is fluidly coupled to a tissue inlet that is proximate a tissue-facing side of the interface body. The reduced-pressure channel extends from the positive-pressure channel to the tissue-facing side of the interface body and is configured to deliver the reduced pressure to the tissue site through the aperture in the flexible film drape. The interface is configured such that the positive-pressure channel is configured to produce the reduced pressure by a Venturi effect as positive pressure flows through the positive-pressure channel and past the reduced-pressure channel. The interface also includes a reduced-pressure-sensing channel that extends from the reduced-pressure-sensing port to the tissue-facing side of the interface body. The system further includes a pressure-sensing unit fluidly coupled to the reduced-pressure-sensing channel for measuring a pressure in the reduced-pressure-sensing channel.

In yet another illustrative embodiment, a system for treating a tissue site on a patient with reduced pressure includes a manifold for placing proximate the tissue site. The manifold has a first side and a second, tissue-facing side. The system further includes a flexible film drape for covering the first side of the manifold to form a sealed space containing the manifold. The flexible film drape has an aperture. The system also includes an interface having a first side and a second, tissue-facing side for positioning over the flexible film drape. The second, tissue-facing side of the interface is disposed on the flexible film drape proximate the manifold. The interface includes an inlet port formed in an interface body for allowing intake of an ambient gas. The inlet port has a first diameter at an upstream end and a second, smaller diameter at an opposing downstream end. The interface body further includes a first and second reduced-pressure channel. The first reduced-pressure channel extends through the interface body from the inlet port to an outlet port. The second reduced-pressure channel is fluidly coupled to the first reduced-pressure channel and extends from the first reduced-pressure channel to the second, tissue-facing side of the interface. The second reduced-pressure channel is configured to deliver the reduced pressure to the tissue site when a fluid is pulled though the inlet port with sufficient flow rate to produce the reduced pressure by way of a Venturi effect. The system further includes a reduced-pressure source fluidly coupled to the outlet port for pulling the fluid through the first reduced-pressure channel. A pressure-sensing unit is fluidly coupled to a pressure-sensing port for monitoring pressure proximate the tissue site In yet another illustrative embodiment, provided is an interface for providing a reduced pressure to a dressing. The interface includes an interface body, an inlet, a positive-pressure channel, a reduced-pressure channel, and a reduced-pressure sensing channel. The interface body has a first side and a second side, and the second side of the interface body is adapted to face the dressing. The inlet is formed proximate the first side of the interface body, and the inlet has a positive-pressure port and a reduced-pressure-sensing port. The positive-pressure channel is adapted to deliver positive pressure. The positive-pressure channel extends through the interface body from the positive-pressure port to a positive-pressure outlet proximate the first side of the interface body. The positive-pressure channel includes a constricted portion configured to provide a pressure drop. The reduced-pressure channel is adapted to deliver the reduced pressure to the dressing. The reduced-pressure channel is fluidly coupled between the positive-pressure channel and the second side of the interface body, and the reduced pressure delivered by the reduced-pressure channel substantially corresponds to the pressure drop. The reduced-pressure-sensing channel is in fluid communication between the reduced-pressure-sensing port and the second side of the interface body.

In yet another illustrative embodiment, provided is a system for treating a tissue site with reduced pressure. The system includes a manifold, a flexible film drape, an interface, a positive-pressure source, and a pressure sensing unit. The manifold is for placing proximate the tissue site, and the manifold comprises an absorbent layer for absorbing liquids from the tissue site. The flexible film drape is for covering the manifold to form a sealed space containing the manifold, and the flexible film drape has an aperture adapted to provide fluid communication with the sealed space. The interface is adapted to be positioned over the flexible film drape, and the interface includes an interface body, an inlet, a positive-pressure channel, a reduced-pressure channel, and a reduced-pressure sensing channel. The interface body has a first side and a second side, and the second side is adapted to face the flexible film drape and to be in fluid communication with the manifold through the aperture. The inlet is formed proximate the first side of the interface body, and the inlet has a positive-pressure port and a reduced-pressure-sensing port. The positive-pressure port is fluidly isolated from the reduced-pressure-sensing port proximate the inlet. The positive-pressure channel is adapted to deliver positive pressure. The positive pressure channel extends through the interface body from the positive-pressure port to a positive-pressure outlet proximate the first side of the interface body. Further, the positive pressure channel includes a constricted portion configured to provide a pressure drop. The reduced-pressure channel is adapted to deliver a reduced pressure to the manifold. The reduced-pressure channel is fluidly coupled between the positive-pressure channel and the second side of the interface body. Further, the reduced pressure delivered by the reduced-pressure channel substantially corresponds to the pressure drop. The reduced-pressure-sensing channel is in fluid communication between the reduced-pressure-sensing port and the second side of the interface body. The positive-pressure source is fluidly coupled to the positive-pressure channel, and the pressure-sensing unit is fluidly coupled to the reduced-pressure-sensing channel for measuring a pressure in the reduced-pressure-sensing channel.

In yet another illustrative embodiment, provided is a system for treating a tissue site with a reduced pressure. The system includes a manifold, a flexible film drape, an interface, a reduced-pressure source, and a pressure-sensing unit. The manifold is for placing proximate the tissue site, and the manifold has a first side and a second side. The second side of the manifold is adapted to face the tissue site The flexible film drape is for covering the first side of the manifold to form a sealed space containing the manifold, and the flexible film drape has an aperture adapted to provide fluid communication with the sealed space. The interface is for positioning over the flexible film drape proximate the aperture, and the interface has a first side and a second side. The second side of the interface is adapted to face the tissue site. The interface includes an inlet port, a first reduced-pressure channel, a second reduced-pressure channel, and a pressure-sensing port. The inlet port is positioned proximate the first side of the interface, and is adapted to intake ambient gas. Further, the inlet port includes a constricted portion having a first diameter at an upstream end and a second diameter at an opposing downstream end. The second diameter is smaller than the first diameter such that the constricted portion is adapted to provide a pressure drop. The first reduced-pressure channel extends through the interface from the inlet port to an outlet port positioned proximate the first side of the interface. The second reduced-pressure channel is adapted to deliver the reduced pressure to the tissue site and is fluidly coupled between the first reduced-pressure channel and the second side of the interface. The reduced pressure delivered by the second reduced-pressure channel substantially corresponds to the pressure drop. The pressure-sensing port is positioned in the second side of the interface, the reduced-pressure source is fluidly coupled to the outlet port, and the pressure-sensing unit is fluidly coupled to the pressure-sensing port for monitoring pressure proximate the tissue site.

Other aspects, features, and advantages of the illustrative embodiments will become apparent with reference to the drawings and detailed description that follow.

DETAILED DESCRIPTION OF ILLUSTRATIVE EMBODIMENTS

In the following detailed description of the illustrative, non-limiting embodiments, reference is made to the accompanying drawings that form a part hereof. These embodiments are described in sufficient detail to enable those skilled in the art to practice the subject matter of this disclosure. Other embodiments may be utilized, and logical, structural, mechanical, electrical, and chemical changes may be made without departing from the scope of this disclosure. To avoid detail not necessary to enable those skilled in the art to practice the embodiments described herein, the description may omit certain information known to those skilled in the art. The following detailed description is provided without limitation and with the scope of the illustrative embodiments being defined by the appended claims.

Figure 1:
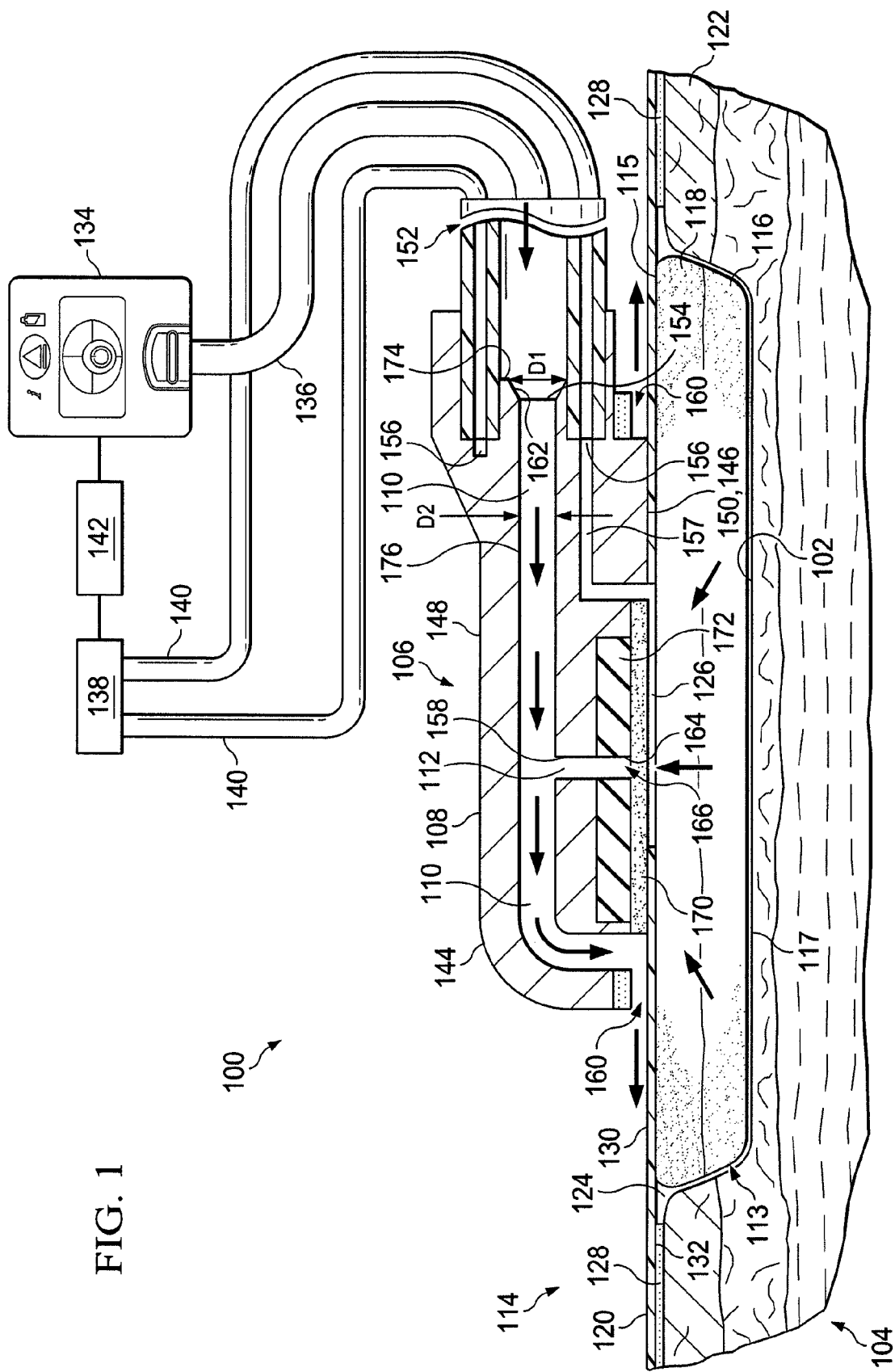
FIG. 1 is a schematic diagram, with a portion shown in cross-section, of an illustrative embodiment of a system for treating a wound on a patient that includes a positive-pressure wound interface configured to produce reduced pressure at the wound by a Venturi effect.
Figure 2:
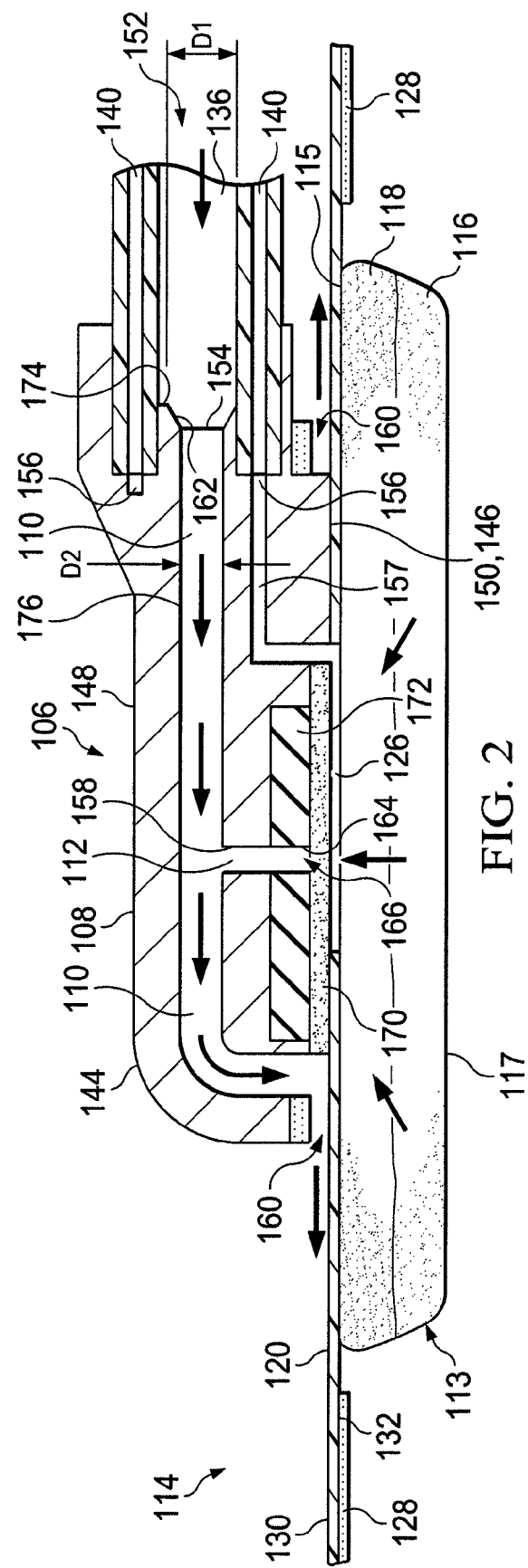
FIG. 2 is a schematic, cross-sectional view of an illustrative embodiment of the positive-pressure wound interface shown in FIG. 1.

Referring to the figures and initially to FIGS. 1-2, provided is a system 100 for treating a tissue site. The tissue site may be, for example, a wound 102 on a patient 104. The system 100 may include a positive-pressure wound interface 106 that has an interface body 108. The interface body 108 may include a positive-pressure channel 110 and a reduced-pressure channel 112. The positive-pressure channel 110 may be configured to create a Venturi effect as positive pressure flows through the positive-pressure channel 110 and past the reduced-pressure channel 112. In this manner, the interface body 108 may enable the delivery of reduced pressure to the wound 102 as the positive pressure flows through the positive-pressure channel 110 and past the reduced-pressure channel 112.

The system 100 may further include a wound dressing 114 positioned adjacent the wound 102. The system 100 may work with many types of dressings, but is shown in FIG. 1, for example, with the wound dressing 114. The wound dressing 114 includes a wound filler 113 that may be comprised of a wound-interface layer 116 and an absorbent layer 118. The wound filler 113 has a first side 115 and a second, tissue-facing side 117. The wound-interface layer 116 may be a manifold, wicking layer, or other material for interfacing with the wound 102. A manifold refers generally to a substance or structure that is provided to assist in applying reduced pressure to, delivering fluids to, or removing fluids from a tissue site, such as the wound 102. The manifold includes a plurality of flow channels or pathways that distribute fluids provided to and removed from the wound 102 around the manifold. In one illustrative embodiment, the flow channels or pathways are interconnected to improve distribution of fluids provided to or removed from the wound 102. The manifold may be a biocompatible material that is capable of being placed in contact with the wound 102 and distributing reduced pressure to the wound 102. Examples of manifolds include, without limitation, one or more of the following: devices that have structural elements arranged to form flow channels, such as, for example, cellular foam, open-cell foam, porous tissue collections, liquids, gels, and foams that include, or cure to include, flow channels; porous material, such as foam, gauze, felted mat, or similar material suited to a particular biological application; porous foam that includes a plurality of interconnected cells or pores that act as flow channels, such as, for example, a polyurethane, open-cell, reticulated foam such as GranuFoam® material manufactured by Kinetic Concepts, Incorporated of San Antonio, Tex.; a bioresorbable material; or a scaffold material.

The absorbent layer 118 may absorb liquid from the wound 102. The absorbent layer 118 may be any material that retains liquids and may comprise one or more of the following: Luquafleece® material, BASF 402c, Technical Absorbents 2317 available from Technical Absorbents (www.techabsorbents.com), sodium polyacrylate super absorbers, cellulosics (carboxy methyl cellulose and salts such as sodium CMC), or alginates. The absorbent layer 118 may allow fluids and exudate removed from the wound 102 to be stored within the wound filler 113 instead of storing the wound fluids remotely in a canister. As will be described in more detail below, the wound dressing 114 may be configured to encourage the evaporation of moisture stored within the wound filler 113 to keep the wound filler 113 from becoming overly saturated with wound fluid. If the wound filler 113 becomes overly saturated with fluid, the wound filler 113 may not be able to absorb additional fluids from the wound 102.

Continuing with FIGS. 1-2, the wound dressing 114 may further include a sealing member 120 disposed over the wound filler 113 and a portion of intact skin 122 to form a sealed space 124. The sealing member 120 may include a first side 130 and a second, tissue facing side 132. A treatment aperture 126 may be formed in the sealing member 120 to provide fluid access to the sealed space 124. The positive-pressure wound interface 106 may be in fluid communication with the treatment aperture 126.

The sealing member 120 may be any liquid-impervious material capable of forming the sealed space 124 into which reduced pressure may be applied. For example, the sealing member 120 may be formed from a high-moisture-vapor-transfer-rate material (high MVTR material) or a drape material that may be a flexible film. "Moisture Vapor Transmission Rate" or "MVTR" represents the amount of moisture that can pass through a material in a given period of time. A high-moisture-vapor-transfer-rate material typically has a moisture vapor transmission rate greater than 300 g/m$^2$ per 24 hours, and more typically 1000 g/m$^2$ per 24 hours or more The sealing member 120 allows vapor to egress from the sealed space 124 through the sealing member 120 to the atmosphere exterior to the wound dressing 114.

The sealing member 120 may comprise one or more of the following: hydrophilic polyurethane; cellulosics; hydrophilic polyamides; an INSPIRE 2301 material from Expopack Advanced Coatings of Wrexham, United Kingdom; a thin, uncoated polymer drape; natural rubbers; polyisoprene; styrene butadiene rubber; chloroprene rubber; polybutadiene; nitrile rubber; butyl rubber; ethylene propylene rubber; ethylene propylene diene monomer; chlorosulfonated polyethylene; polysulfide rubber; polyurethane (PU); EVA film; co-polyester; silicones; silicone drape; a 3M Tegaderm® drape; a polyurethane (PU) drape, such as one available from Avery Dennison Corporation of Pasadena, Calif.; polyether block polyamide copolymer (PEBAX), for example, from Arkema, France; or other similar material.

An attachment device 128, for example, an adhesive, may be coupled to all or a portion of a second, patient-facing side 132 of the sealing member 120. The attachment device 128 may attach the sealing member 120 to the portion of intact skin 122 of the patient 104 and/or a portion of the wound filler 113.

The performance of the sealing member 120 with respect to MVTR may be enhanced by only covering a limited surface area of the second, patient-facing side 132 of the sealing member 120 with the attachment device 128. For example, only the peripheral edge or portion of the sealing member 120 may be covered, or a limited pattern may be used. According to one illustrative embodiment of a limited pattern, only 30 to 60 percent of the surface area of the second, patient-facing side 132 may be covered with the attachment device 128. For example, the attachment device 128 may be applied on the second, patient-facing side 132 in a limited pattern, such as, for example, a grid, spaced dots, swirls, or other patterns. The positive pressure wound interface 106 may be coupled to the first side 130 of the sealing member 120 by any of the previously mentioned coupling techniques, or other similar techniques.

Continuing with FIGS. 1-2, the system 100 may further include a positive-pressure source 134 fluidly coupled to the positive-pressure wound interface 106 such that the positive-pressure wound interface 106 may receive positive pressure from the positive-pressure source 134. A positive-pressure conduit 136 may couple the positive-pressure source 134 to the positive-pressure wound interface 106. The positive-pressure conduit 136 may be coupled by bonding, tube locks, interference fit, or other technique to the positive-pressure wound interface 106. Although FIG. 1 illustrates the positive-pressure conduit 136 coupling the positive-pressure wound interface 106 to the positive-pressure source 134, the positive-pressure source 134 may be an integral part of the wound dressing 114. Thus, in some embodiments, the positive-pressure conduit 136 may be optional. The positive-pressure source 134 may be any device for supplying positive pressure, such as, for example, a positive-pressure pump. In specific, non-limiting examples, the positive-pressure source 134 may be a diaphragm pump or a disc-pump. In one embodiment (not shown), a disc-pump may be positioned adjacent or within the wound dressing 114. In another embodiment (not shown), the disc-pump may be an integral part of the wound dressing 114.

In one embodiment, the positive-pressure source 134 may be capable of delivering a flow rate between about 0.1 L/Min. to about 4 L/min. In a specific, non-limiting embodiment, the positive-pressure source 134 may be capable of providing a flow rate of about 3 L/min when the positive-pressure source 134 is not connected to the positive-pressure wound interface 106, and a flow rate of about 1 L/Min. to about 1.5 L/min at 50 mm Hg when the positive-pressure source 134 is connected to the positive-pressure wound interface 106. In the above embodiments, the flow rate provides a fluid speed necessary to obtain the desired reduced pressure using the Venturi effect.

The amount and nature of the positive pressure supplied to the positive-pressure wound interface 106 may vary depending on the construction of the positive-pressure wound interface 106 and the desired amount or nature of the reduced pressure being supplied to the wound 102. The desired reduced pressure supplied to the wound 102 may be between about −5 mm Hg (−667 Pa) to about −500 mm Hg (−66.7 kPa), and more specifically between about −75 mm Hg (−9.9 kPa) to about −300 mm Hg (−39.9 kPa). The positive pressure may be supplied continuously or intermittently, causing the reduced pressure to be applied to the wound 102 either continuously or intermittently.

The positive-pressure source 134 may be housed within or used in conjunction with a pressure sensing unit 138. The positive-pressure source 134 and the pressure sensing unit 138 may comprise a therapy unit. The pressure sensing unit 138 may contain sensors, processing units, alarm indicators, memory, databases, software, display units, and user interfaces that further facilitate the application of reduced pressure treatment to the wound 102. In one example, pressure-detection sensors (not shown) located in the pressure sensing unit 138 may receive pressure data from the positive-pressure wound interface 106 via one or more sensing lumens 140. The sensing lumens 140 may be dedicated to delivering reduced pressure data to the pressure-detection sensors. The pressure-detection sensors may communicate with a processing unit, or controller 142. The controller 142 may monitor and control the reduced pressure delivered to the wound 102 by controlling, for example, the flow rate from the positive pressure source 134.

Referring now primarily to FIG. 2, but with reference to FIG. 1, the positive-pressure wound interface 106 has a first side 144 and a second, tissue-facing side 146. The second, tissue-facing side 146 of the positive-pressure wound interface 106 may be disposed on the sealing member 120 proximate the treatment aperture 126. As described above, the positive-pressure wound interface 106 may be comprised of the interface body 108. The interface body 108 has a first side 148 and a second, tissue-facing side 150. The positive pressure wound interface 106 may be a single, molded piece made from flexible, stable polymers such as silicones, polyurethane (PU), rubber, or similar materials. In another embodiment, the positive-pressure wound interface 106 may be assembled from two parts, each part being a different material. An inner part may be comprised of a rigid polymer such as an acrylonitrile butadiene styrene (ABS) or a polycarbonate acrylonitrile butadiene styrene(PC/ABS). An outer part may be positioned around a portion of the inner part. The outer part may be comprised of one of the flexible polymers described above, such as silicones, PU, or rubber. The positive-pressure wound interface 106 may be assembled from two parts as described above to help the positive-pressure wound interface 106 from deforming under thermal and pressure changes. Portions of the positive-pressure wound interface 106 subject to air flow may have surfaces that are smooth and substantially free of molding inclusions to avoid air turbulences.

An inlet 152 may be formed within the interface body 108. The inlet 152 may include a positive-pressure port 154 and a reduced-pressure-sensing port 156 that are fluidly isolated from each other at least proximate the inlet 152. The positive-pressure port 154 may be in fluid communication with, or fluidly coupled to, the positive-pressure conduit 136. The reduced-pressure-sensing port 156 may be in fluid communication, with or fluidly coupled to, the one or more sensing lumens 140 by way of a reduced-pressure-sensing channel 157.

The positive-pressure channel 110 extends through the interface body 108 from the positive-pressure port 154 to a positive-pressure outlet 160. The positive-pressure channel 110 may have a longitudinal axis substantially parallel to the surface of the wound 102, or at an angle to the surface of the wound 102, when positioned for use. The positive-pressure channel 110 may be configured to deliver the positive pressure through the interface body 108 from the positive-pressure port 154 downstream to the positive-pressure outlet 160. The positive-pressure channel 110 may have a surface that is smooth and substantially free of molding inclusions to avoid air turbulences within the positive-pressure channel 110.

In another embodiment, the positive-pressure channel 110 may be in fluid communication with a plurality of positive-pressure outlets 160 for directing flow circumferentially about the interface body 108 and over the sealing member 120, as described further below. In yet another embodiment, the positive-pressure outlet 160 may be a single outlet, such as a circumferential outlet, circumscribing the interface body 108 for providing circumferential flow.

To utilize the Venturi effect as desired, the positive-pressure channel 110 may include at least one constricted portion 162. In a specific, non-limiting embodiment, the at least one constricted portion 162 may have a slope of approximately 20, 25, 30, or 40 degrees (and any number of degrees thereinbetween) relative to the longitudinal axis of the positive-pressure channel 110 or the longitudinal axis of the constricted portion 162. The slope of the at least one constricted portion 162 may be gradual to avoid air turbulence within the positive-pressure channel 110 for a given set of operational parameters such as, for example, air flow velocity and pressures. The positive-pressure channel 110 may be configured to create a Venturi effect when experiencing sufficient fluid flow therethrough. The Venturi effect is a jet effect that results in a reduction in pressure when the velocity of an air flow increases due to the principles of continuity. When a high flow fluid, for example air, is subjected to a constriction, the velocity of the air increases. In order to maintain the principles of conservation of energy and mass, however, the air pressure must decrease in response to the increase in velocity. Therefore, the positive-pressure wound interface 106 as a whole, including the positive-pressure channel 110, is configured to take advantage of the Venturi effect to create a reduced pressure that may be applied to the wound 102 via the reduced-pressure channel 112.

The at least one constricted portion 162 of the positive-pressure channel 110 may be cone shaped with a first end 174 having a first diameter, D1, and a second, opposing end 176 having a second diameter, D2, such that the first diameter, D1, is larger than the second diameter, D2. In a specific, non-limiting example, the first diameter, D1, may be between about 5 millimeters to about 10 millimeters (mm), and the second diameter, D2, may be between about 0.2 mm to about 0.7 mm. The at least one constricted portion 162 may be formed in any suitable shape capable of inducing the Venturi effect and minimizing air turbulence within the positive-pressure wound interface 106, as described above.

Bernoulli's equation may be used to optimize the construction of the positive-pressure wound interface 106. For example, Bernoulli's equation may be used to calculate the pressure drop for a given construction of the positive-pressure wound interface 106. The pressure drop may correspond to the amount of reduced pressure applied to the wound 102. Bernoulli's equation may be represented as follows: $p_1 - p_2 = \rho/2(v_2^2 - v_1^2)$, where $\rho$ is the density of the air, v1 may be the velocity of the air as it enters the at least one constricted portion 162, and v2 may be the velocity of the air as it exits the at least one constricted portion 162. Therefore, the configuration of the positive-pressure wound interface 106 may be modified so that a desired pressure drop, p1-p2, is reached.

The reduced-pressure channel 112 may be fluidly coupled to the positive-pressure channel 110 such that the reduced-pressure channel 112 is in fluid communication with the positive-pressure channel 110. The reduced-pressure channel 112 may include a first end 158 fluidly coupled to the positive-pressure channel 110 and a second, tissue-facing end 164 fluidly coupled to a tissue inlet 166. The tissue inlet 166 may be proximate the second, tissue-facing side 150 of the interface body 108. The reduced-pressure channel 112 may extend from the positive-pressure channel 110 to the tissue-facing side 150 of the interface body 108. In one embodiment, the reduced-pressure channel 112 may be coupled to the positive-pressure channel 110 downstream of the at least one constricted portion 162. In another embodiment, the reduced-pressure channel 112 may be coupled to the positive-pressure channel 110 at the at least one constricted portion 162. In a specific, non-limiting embodiment, the longitudinal dimension of the reduced-pressure channel 112, which extends from the positive-pressure channel 110 to the tissue-facing side 150 of the interface body 108, may be greater than about 15 millimeters (mm). In other non-limiting embodiments, the longitudinal dimension may be between about 5 mm to about 20 mm. The reduced-pressure channel 112 may be substantially perpendicular to the longitudinal axis of the positive-pressure channel 110. The reduced-pressure channel 112 may be configured to deliver reduced pressure to the wound 102 when positive pressure is pushed into the positive-pressure channel 110 and past the reduced-pressure channel 112 at an adequate speed. The reduced-pressure channel 112 may have a surface that is smooth and substantially free of molding inclusions to avoid air turbulences within the positive-pressure wound interface 106.

The positive-pressure wound interface 106 may be configured so that air flowing through the positive-pressure channel 110 entrains air, including air from the reduced-pressure channel 112, that is then vented through the positive-pressure outlet 160. The positive-pressure outlet 160 may be configured to direct air flow circumferentially over the first side 130 of the sealing member 120 to enhance the moisture-vapor-transmission rate of the sealing member 120. As previously mentioned, enhancing the moisture-vapor-transmission rate may increase the life of the wound filler 113 by keeping the wound filler 113 from becoming saturated with wound fluid. In one embodiment, the positive-pressure outlet 160 may be configured to vent directly to the atmosphere. In another embodiment, one or more ducts 168 (see FIGS. 3-5), which may include conduits, baffling, or other elements, may be coupled to the positive-pressure outlet 160 for further directing positive flow over the first side 130 of the sealing member 120. The one or more ducts 168 may include or be attached to a Coanda device as will be described in more detail below with reference to FIGS. 3-5.

The wound dressing 114 may further comprise a hydrophobic filter 170 positioned adjacent the tissue inlet 166 for preventing wound exudate from entering the reduced-pressure channel 112. In another embodiment, the hydrophobic filter 170 may be fluidly coupled anywhere in the reduced-pressure channel 112.

In one embodiment, a regulating valve 172 may be associated with the reduced pressure channel 112 for regulating the amount of reduced pressure being supplied to the wound 102 independently of the air speed in the positive-pressure chamber 110. The regulating valve 172 may provide pressure regulation at the wound 102 that is independent of the pressure in the positive-pressure channel 110.

In another embodiment, the controller 142 may be used to vary the amount of positive pressure provided by, for example, the positive pressure source 134, to control the amount of reduced pressure applied at the wound 102. The controller 142 may receive feedback from the pressure sensing unit 138 that indicates the amount of pressure being applied to the wound 102. Based on the feedback, the controller 142 may signal the positive-pressure source 134 to vary or modulate the amount of positive pressure generated by the positive-pressure source 134 so that the reduced pressure applied to the wound 102 reaches a desired level. Power provided to the positive-pressure source 134 may be varied or modulated to vary the amount of positive pressure generated by the positive pressure source 134. A control valve (not shown) may also be utilized to vary the amount of positive pressure. The controller 142 may allow the system 100 to operate over a range of desired reduced pressure levels. The controller 142 may be configured to operate at a number of preset reduced pressure levels that may be selected by or provided to a healthcare provider. The controller 142 may improve the efficiency of the positive-pressure source 134 by modulating power to the positive pressure source 134 based on the desired amount of positive pressure to be generated. In the instance that a battery is used to power the positive-pressure source 134, the battery life may be extended in this manner.

The controller 142 may be coupled to an atmospheric pressure sensor (not shown). The atmospheric pressure may vary depending on various elements, including the altitude in which the system 100 is operating. The effects of variable atmospheric pressure may affect the performance of the system 100. The atmospheric pressure sensor may allow the controller 142 to account for variances in the atmospheric pressure and signal or command the positive-pressure source 134 accordingly. In other words, the controller 142 may signal the positive-pressure source 134 to increase or decrease the pressure output based on variances in atmospheric pressure.

Figure 3:
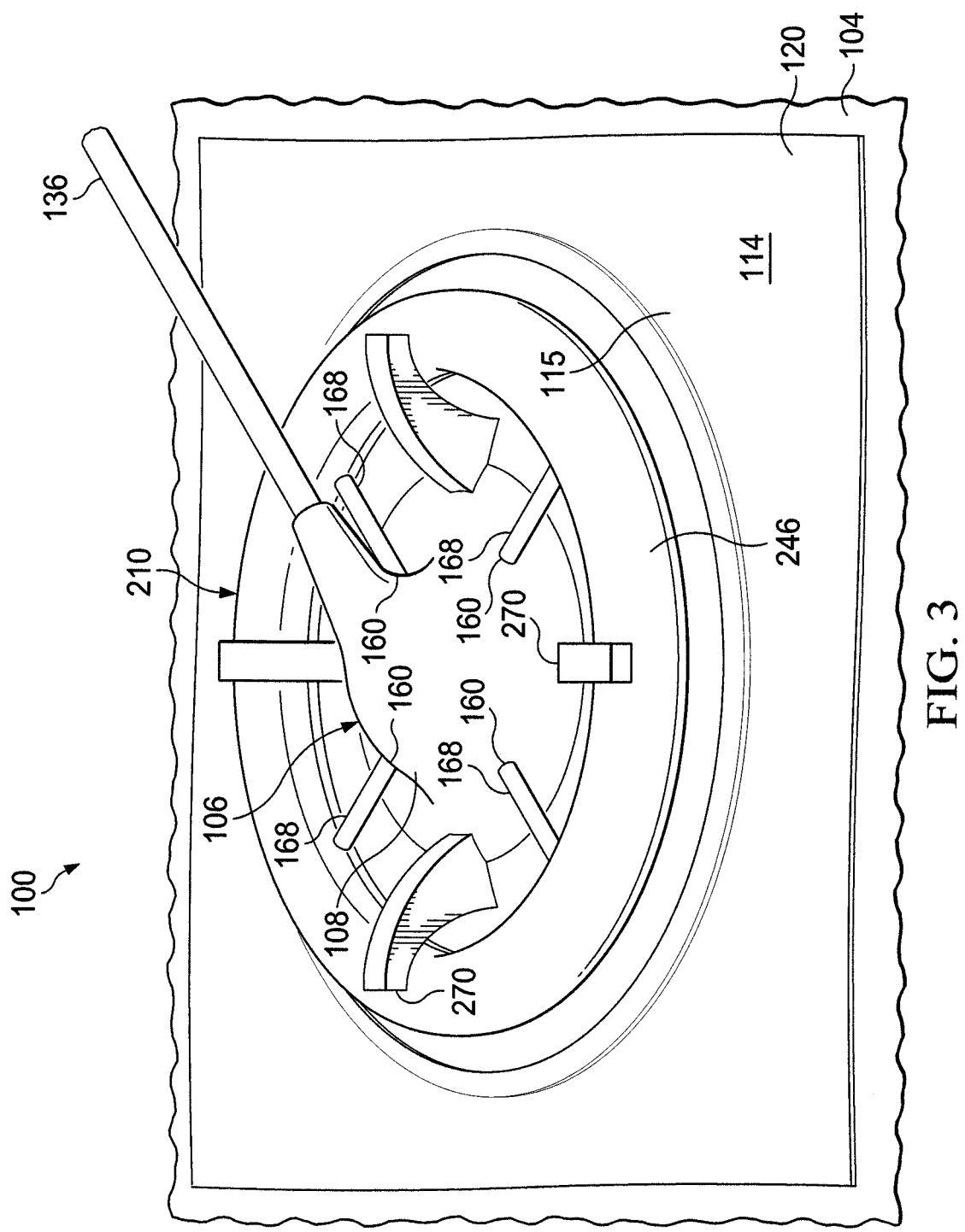
FIG. 3 is a schematic, perspective view of an illustrative embodiment of a portion of a system for treating a wound on a patient that includes a positive-pressure wound interface and a Coanda device.
Figure 4:
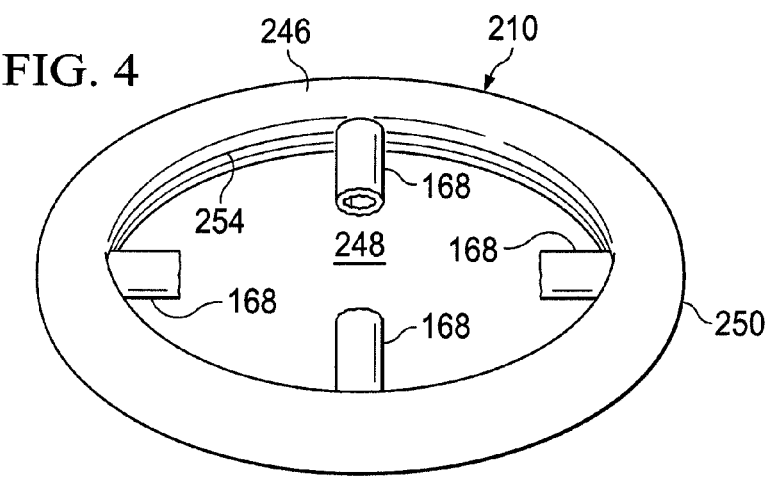
FIG. 4 is a schematic, perspective view of an illustrative embodiment of a Coanda device.
Figure 5:
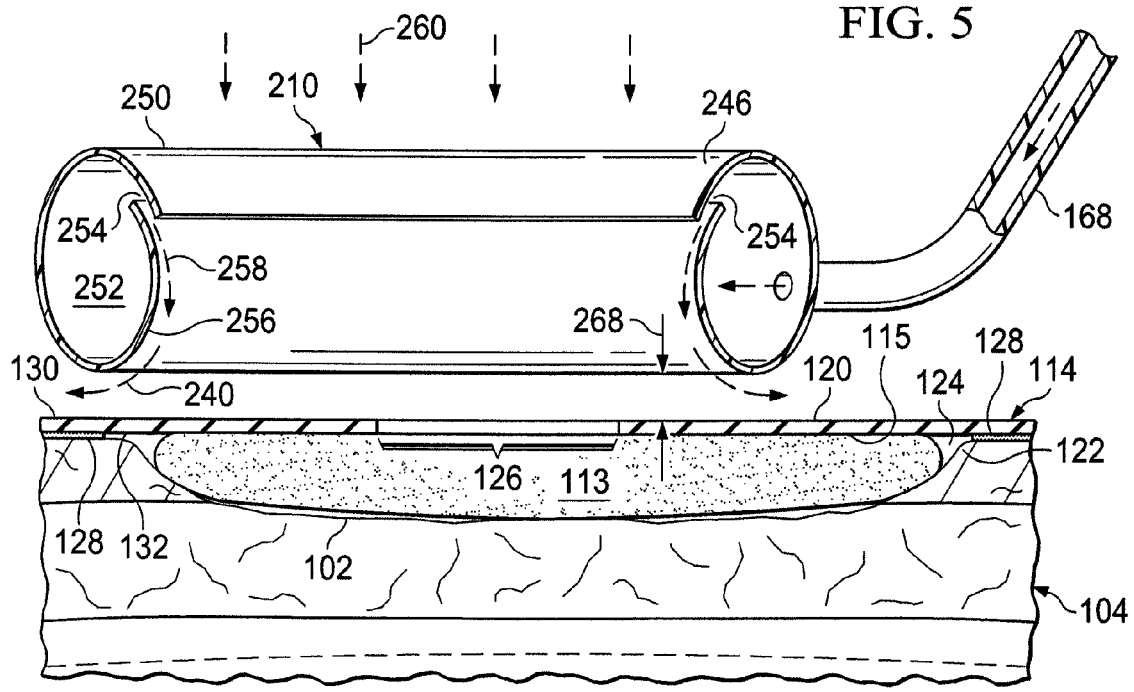
FIG. 5 is a schematic, perspective view, of a portion of the Coanda device of FIG. 4 shown over a wound.

Referring now primarily to FIGS. 3-5, the system 100 illustrated in FIG. 1 may further include a Coanda device 210 associated with the positive-pressure wound interface 106. The Coanda device 210 may receive fluid exiting the positive-pressure wound interface 106 to encourage airflow over the wound dressing 114 for enhancing evaporation of liquids from the wound dressing 114. Among other benefits, enhanced evaporation of liquids from the wound dressing 114 may allow the wound dressing 114 to process relatively more fluids. The positive-pressure wound interface 106 and the Coanda device 210 may be associated with one another in several ways. For example, the positive-pressure wound interface 106 may be coupled to the Coanda device 210, formed integrally with the Coanda device 210, or placed adjacent to the Coanda device 210. The Coanda device 210 may be coupled to the positive pressure outlet 160 of the positive-pressure wound interface 106 by the one or more ducts 168.

In other embodiments, other entrainment devices may be used as the Coanda device 210 to entrain air and direct the air over the wound dressing 114 to achieve the desired air-flow. These other entrainment devices, such as, for example, a Conventional Ejector, may be used to entrain air to create a more voluminous flow based on the presence of a high pressure flow. The Conventional Ejector may utilize a primary flow located proximate to an available secondary air source that is "dragged" by an airfoil shape to have the effect of an air-multiplier.

The Coanda device 210 may be a device for entraining air, as described above, that utilizes the Coanda effect. The Coanda effect is generally a phenomena in which a flow attaches itself to a nearby surface and remains attached even as the surface (Coanda surface) pulls away from the initial direction of the flow. As the flow curves away, the flow may entrain surrounding fluids and increase the volume of the flow. The Coanda surface close to the flow may restrict the entrainment in that region, and as the flow accelerates to try to balance a momentum transfer, a pressure differential may develop across the flow that changes or deflects the direction of the flow closer to the surface. The Coanda effect is named for Henri Coanda and the concept is described in U.S. Pat. No. 2,052,869, granted to Coanda.

Thus, as shown in FIG. 5, the Coanda device 210 creates a desired airflow as suggested by arrows 240. The Coanda device 210 may be fluidly coupled by the one or more ducts 168 to the positive-pressure outlet 160 formed in the positive-pressure wound interface 106. The positive-pressure outlet 160 may supply a relatively high pressure air to the Coanda device 210. In one embodiment, the discharge flow rate exiting the positive-pressure outlet 160 may be approximately 2 L/min or greater. As used herein, air is intended to cover other working gases that may be used to help remove moisture. The Coanda device 210 may receive positive pressure air from the one or more ducts 168 and develop an enhanced air flow that is delivered from the Coanda device 210 over the first side 130 of the sealing member 120. As the air moves across the wound dressing 114, any moisture or vapor on the first side 130 of the sealing member 120 may be removed. This may increase or maintain a strong relative humidity gradient across the sealing member 120 that helps remove liquid from the wound dressing 114, which may enhance the ability of the wound dressing 114 to process liquids.

Continuing with FIGS. 3-5, the Coanda device 210 may include an annular nozzle 246. The annular nozzle 246 may form a central opening 248. The central opening 248 may surround much of the interface body 108 and a portion of the interface body 108 may extend through the central opening 248. The annular nozzle 246 may have walls 250 that form an interior passage 252. A nozzle opening 254 may be formed on the annular nozzle 246 on a portion in or near the central opening 248. A portion of the walls 250 may form a Coanda surface 256 proximate to and downstream from the nozzle opening 254. The fluid or air exiting the nozzle opening 254 may entrain additional fluid from the central opening 248 as the air flow follows the Coanda surface 256. The flow of air from the nozzle opening 254 plus the entrained air from the central opening 248 may produce a combined fluid flow.

For the configuration shown in FIG. 5, air may be moved out of the nozzle opening 254 as suggested by arrows 258. The airflow may entrain additional air from the central opening 248 as suggested by arrows 260. The combined fluid flow is suggested by the arrows 240. Based on the Coanda effect, if a volume $V_1$ of air is delivered by the one or more ducts 168 to the Coanda device 210 over a time T, and a volume $V_2$ of air is delivered through the central opening 248 of the Coanda device 210 over the time T, the combined air flow $(V_2+V_1)$ will be enhanced or more voluminous than the original supply $(V_1)$. The Coanda device 210 may operate as described in various positions, and thus, the positioning depicted in FIGS. 3-5 may be may be flipped or rotated for orienting the nozzle opening 254 to discharge air away from a base portion of the interface body 108 such that air recruited from the central opening 248 is pulled from proximate the first side 130 of the sealing member 120.

A number of devices or elements may be used to position the Coanda device 210 to have a flow clearance 268 between the Coanda device 210 and the sealing member 120. For example, referring to FIG. 3, a plurality of rib members 270 may be used to suspend the annular nozzle 246 of the Coanda device 210 to create the flow clearance 268.

Figure 6:
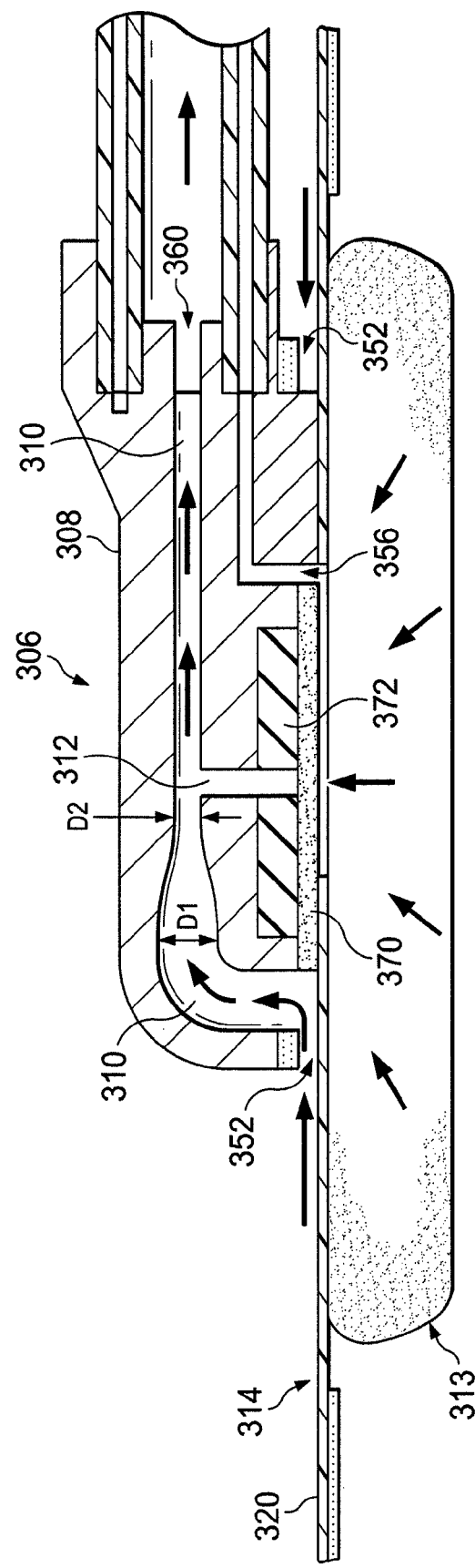
FIG. 6 is a schematic, cross-sectional view of an illustrative embodiment of a wound interface for use in a system for treating a wound on a patient that utilizes a Venturi effect to deliver a reduced pressure to the wound.

Referring now primarily to FIG. 6, presented is a reduced-pressure wound interface 306 for use with a reduced-pressure source (not shown). The reduced-pressure source may be analogous to the positive-pressure source 134, but adapted to provide reduced-pressure. The reduced-pressure wound interface 306 and the reduced-pressure source may be part of a reduced-pressure treatment system used to treat a wound with reduced pressure. The reduced-pressure wound interface 306 may be analogous in many respects to the positive-pressure wound interface 106 illustrated in FIG. 1. Namely, the reduced-pressure wound interface 306 may be configured to create a Venturi effect that develops the reduced pressure at a wound. The reduced-pressure wound interface 306 may have an interface body 308 that may include a first reduced-pressure channel 310 and a second reduced-pressure channel 312. The first reduced-pressure channel 310 may be configured to create a Venturi effect as air is pulled through the first reduced-pressure channel 310 and past the second reduced-pressure channel 312. Air may be pulled through the first reduced-pressure channel 310 by the reduced-pressure source. The interface body 308 may enable the delivery of reduced pressure to the wound as the air flows through the first reduced-pressure channel 310 and past the second reduced-pressure channel 312.

A wound dressing 314, analogous to the wound dressing 114 of FIG. 1, may be positioned adjacent the wound. Similar to the wound dressing 114, the wound dressing 314 may include a wound filler 313 that may be comprised of a wound-interface layer and an absorbent layer (not shown). The wound-interface layer may be a manifold as described above. In one embodiment, the wound filler 313 may be a manifold only since liquids may be removed directly as described herein. The wound filler 313 may be covered by a sealing member 320. The sealing member 320 may be formed from a high-moisture-vapor-transfer-rate material (high MVTR material) or a drape material that may be a flexible film.

The amount, nature, or pressure of the air pulled through the first reduced-pressure channel 310 may vary depending on the construction of the reduced-pressure wound interface 306, ambient conditions, and the desired amount of the reduced pressure being supplied to the wound. The desired reduced pressure supplied to the wound may be between about −5 mm Hg (−667 Pa) to about −500 mm Hg (−66.7 kPa), and more specifically between about −75 mm Hg (−9.9 kPa) to about −300 mm Hg (−39.9 kPa). The reduced-pressure source may cause air to be pulled through the first reduced-pressure channel 310 either continuously or intermittently, causing the reduced pressure to be applied to the wound either continuously or intermittently.

The reduced-pressure source may be housed with or used in conjunction with a pressure-sensing unit (not explicitly shown but analogous to the pressure sensing unit 138 in FIG. 1). The pressure-sensing unit may be fluidly coupled to a pressure-sensing port 356 formed in the interface body 308 such that the pressure-sensing port 356 has an opening adjacent a tissue-facing side of the interface body 308. The pressure-sensing unit may receive a pressure sample from the pressure-sensing port 356 for monitoring pressure at the wound. A controller may be connected to the sensing unit and the reduced-pressure source. The controller may send signals or commands to the reduced-pressure source based on data received from the sensing unit to regulate the amount of reduced pressure supplied to the wound.

An inlet port 352 may be formed within the interface body 308. The inlet port 352 may allow the intake of an ambient gas. The inlet port 352 may be shaped such that the inlet port 352 has a first diameter, D1, at an upstream end, and a second diameter, D2, at an opposing, downstream end. The first diameter, D1, may be larger than the second diameter, D2. In other words, the inlet port 352 may have a constricted portion defined by the first and the second diameters, D1 and D2. The inlet port 352 may have a slope of approximately 20, 25, 30, 35, or 40 degrees (and any number of degrees thereinbetween) relative to a longitudinal axis of the first reduced-pressure channel 310 or the longitudinal axis of the constricted portion.

The first reduced-pressure channel 310 may extend through the interface body 308 from the inlet port 352 to an outlet port 360. The first reduced-pressure channel 310 may have a longitudinal axis that is substantially parallel to the surface of the wound, or at an angle to the surface of the wound, when positioned for use. The first reduced-pressure channel 310 may be configured to pull air through the interface body 308 from the inlet port 352 downstream to the outlet port 360. The first reduced-pressure channel 310 may have a surface that is smooth and substantially free of molding inclusions to avoid air turbulences within the first reduced-pressure channel 310.

The second reduced-pressure channel 312 may be coupled to the first reduced-pressure channel 310 such that the second reduced-pressure channel 312 is in fluid communication with the first reduced-pressure channel 310. The second reduced-pressure channel 312 may extend from the first reduced-pressure channel 310 to the tissue-facing side of the reduced-pressure wound interface 306. The second reduced-pressure channel 312 may be configured to deliver reduced pressure to the wound when a fluid or air is pulled through the inlet port 352 with sufficient flow rate to produce the reduced pressure at the wound by way of the Venturi effect. In one embodiment, the second reduced-pressure channel 312 may be coupled to the first reduced-pressure channel 310 downstream of the constricted portion. In another embodiment, the second reduced-pressure channel 312 may be coupled to the first reduced-pressure channel 310 at the constricted portion. In a specific, non-limiting embodiment, the longitudinal dimension of the second reduced-pressure channel 312, which extends from the first reduced-pressure channel 310 to the tissue-facing side of the interface body 308, may be greater than 15 millimeters (mm). In other non-limiting embodiments, the longitudinal dimension may be between about 5 mm to about 20 mm. The second reduced-pressure channel 312 may be substantially perpendicular to, or at an angle to, the longitudinal axis of the first reduced-pressure channel 310. The second reduced-pressure channel 312 may have a surface that is smooth and substantially free of molding inclusions to avoid air turbulences within the interface 306.

The reduced-pressure wound interface 306 may be configured so that air pulled into the first reduced-pressure channel 310 via the inlet port 352 entrains air surrounding the sealing member 320. The air flow caused by the air being pulled into the inlet port 352 may cause air to flow over the sealing member 320 to enhance the moisture-vapor-transmission rate of the sealing member 320. As previously mentioned, enhancing the moisture-vapor-transmission rate may increase the life of the wound filler 313 by keeping the wound filler 313 from becoming overly saturated with wound fluid.

The wound dressing 314 may further comprise a hydrophobic filter 370 positioned between the wound and the first reduced-pressure channel 310. In one embodiment, the hydrophobic filter 370 may be positioned within the second reduced-pressure channel 312. In another embodiment, no hydrophobic filter may be used and wound exudate removed from the wound may be pulled through the first and second reduced-pressure channels 310, 312 and deposited in a canister (not shown).

In one embodiment, a regulating valve 372 may be associated with the second reduced-pressure channel 312 for regulating the amount of reduced pressure being supplied to the wound. The regulating valve 372 may provide pressure regulation at the wound that is independent of the reduced pressure in the first reduced-pressure channel 310.

The above description of illustrative embodiments is given by way of example. Although various embodiments have been described above with a certain degree of particularity, or with reference to one or more individual embodiments, modifications may be made by those skilled in the art without departing from the scope of the appended claims. Further, the steps of the methods described herein may be carried out in any suitable order, or simultaneously where appropriate. Aspects of any of the embodiments described above may be combined with aspects of any of the other embodiments described to form further examples having comparable or different properties and addressing the same or different problems. Thus, the benefits and advantages described above may relate to one embodiment or may relate to several embodiments.

I claim:

1. An interface for providing a reduced pressure to a dressing, the interface comprising:
   an interface body having a first side and a second side, the second side adapted to face the dressing;
   an inlet formed proximate the first side of the interface body, the inlet having a positive-pressure port and a pressure-sensing port;
   a positive-pressure channel adapted to deliver positive pressure and extending through the interface body from the positive-pressure port to a positive-pressure outlet proximate the first side of the interface body, wherein the positive-pressure channel includes a constricted portion configured to provide a pressure drop;
   a reduced-pressure channel adapted to deliver the reduced pressure to the dressing, the reduced-pressure channel fluidly coupled between the positive-pressure channel and the second side of the interface body, wherein the reduced pressure substantially corresponds to the pressure drop, and wherein the reduced-pressure channel is fluidly coupled to the positive-pressure channel downstream of the constricted portion and between the constricted portion and the positive-pressure outlet; and
   a pressure-sensing channel in fluid communication between the pressure-sensing port and the second side of the interface body.

2. The interface of claim 1, wherein the reduced-pressure channel has a longitudinal dimension extending between the positive-pressure channel and the second side of the interface body that is greater than 15 millimeters.

3. The interface of claim 1, wherein the positive-pressure channel has a longitudinal axis substantially parallel to the second side of the interface body, and wherein the reduced-pressure channel is substantially perpendicular to the positive-pressure channel.

4. The interface of claim 1, further comprising a hydrophobic filter positioned adjacent the second side of the interface body and adapted to be positioned in fluid communication between the reduced-pressure channel and the dressing.

5. The interface of claim 1, further comprising a regulating valve associated with the reduced-pressure channel that is adapted to regulate an amount of the reduced pressure being delivered to the dressing.

6. The interface of claim 1, further comprising at least one duct in fluid communication with the positive-pressure outlet, wherein the at least one duct is configured to direct flow over a drape.

7. The interface of claim 1, wherein the constricted portion has a first diameter at an upstream end and a second diameter at an opposing downstream end, the second diameter being smaller than the first diameter, and wherein the constricted portion has a slope of 30 degrees relative to a longitudinal axis of the positive-pressure channel.

8. The interface of claim 1, wherein the positive-pressure outlet is configured to vent to the atmosphere.

9. The interface of claim 1, wherein the reduced-pressure channel is fluidly coupled to the positive-pressure channel at the constricted portion.

10. The interface of claim 1, further comprising:
    a hydrophobic filter disposed proximate the second side of the interface body;
    a regulating valve associated with the reduced-pressure channel that is adapted to regulate an amount of the reduced pressure being delivered to the dressing;
    at least one duct associated with the positive-pressure outlet and configured to direct flow over a drape;
    wherein the reduced-pressure channel has a longitudinal dimension extending between the positive-pressure channel and the second side of the interface body that is greater than 15millimeters;
    wherein the positive-pressure channel has a longitudinal axis substantially parallel to the second side of the interface body, and wherein the reduced-pressure channel is substantially perpendicular to the positive-pressure channel;
    wherein the constricted portion has a slope greater than 20 degrees relative to a longitudinal axis of the positive-pressure channel;
    wherein the positive-pressure outlet is configured to vent to atmosphere; and
    wherein the positive-pressure port is fluidly isolated from the pressure-sensing port proximate the inlet.

11. A system for treating a tissue site with reduced pressure, comprising:
    a manifold for placing proximate the tissue site, the manifold comprising an absorbent layer for absorbing liquids from the tissue site;
    a flexible film drape for covering the manifold to form a sealed space containing the manifold, the flexible film drape having an aperture adapted to provide fluid communication with the sealed space;
    an interface adapted to be positioned over the flexible film drape;
    wherein the interface comprises:
      an interface body having a first side and a second side, the second side adapted to face the flexible film drape and to be in fluid communication with the manifold through the aperture,
      an inlet formed proximate the first side of the interface body, the inlet having a positive-pressure port and a pressure-sensing port, wherein the positive-pressure port is fluidly isolated from the pressure-sensing port proximate the inlet,
      a positive-pressure channel adapted to deliver positive pressure and extending through the interface body from the positive-pressure port to a positive-pressure outlet proximate the first side of the interface body, wherein the positive-pressure channel includes a constricted portion configured to provide a pressure drop, a reduced-pressure channel adapted to deliver a reduced pressure to the manifold, the reduced-pressure channel fluidly coupled between the positive-pressure channel and the second side of the interface body, wherein the reduced pressure substantially corresponds to the pressure drop, and a pressure-sensing channel in fluid communication between the pressure-sensing port and the second side of the interface body;

a positive-pressure source fluidly coupled to the positive-pressure channel; and a pressure-sensing unit fluidly coupled to the pressure-sensing channel for measuring a pressure in the pressure-sensing channel.

12. The system of claim 11, further comprising at least one duct fluidly coupled to the positive-pressure outlet for directing positive flow over the flexible film drape.

13. The system of claim 12, wherein the at least one duct comprises a Coanda device adapted to entrain air and to increase a volume of the positive flow.

14. The system of claim 11, further comprising a controller coupled to the positive-pressure source for regulating an amount of the positive pressure delivered to the positive-pressure port.

15. The system of claim 11, wherein the reduced-pressure channel has a longitudinal dimension extending between the positive-pressure channel and the second side of the interface body that is greater than 15 millimeters.

16. The system of claim 11, wherein the positive-pressure channel has a longitudinal axis that is substantially parallel to the second side of the interface body, and wherein the reduced-pressure channel is substantially perpendicular to the positive-pressure channel.

17. The system of claim 11, further comprising a hydrophobic filter positioned adjacent the second side of the interface body and adapted to be positioned in fluid communication between the reduced-pressure channel and the manifold.

18. The system of claim 11, further comprising a regulating valve associated with the reduced pressure channel that is adapted to regulate an amount of the reduced pressure being delivered to the tissue site.

19. The system of claim 11, wherein the constricted portion has a first diameter at an upstream end and a second diameter at an opposing downstream end, the second diameter being smaller than the first diameter, and wherein the at least one constricted portion has a slope of 30 degrees relative to a longitudinal axis of the positive-pressure channel.

20. The system of claim 11, wherein the positive-pressure outlet is configured to vent to the atmosphere.

21. The system of claim 11, wherein the reduced-pressure channel is fluidly coupled to the positive-pressure channel downstream of the at least one constricted portion and between the constricted portion and the positive-pressure outlet.

22. The system of claim 11, wherein the reduced-pressure channel is fluidly coupled to the positive-pressure channel at the at least one constricted portion.

23. An interface for providing a reduced pressure to a dressing, the interface comprising:

an interface body having a first side and a second side, the second side adapted to face the dressing;

an inlet formed proximate the first side of the interface body, the inlet having a positive-pressure port and a pressure-sensing port;

a positive-pressure channel adapted to deliver positive pressure and extending through the interface body from the positive-pressure port to a positive-pressure outlet proximate the first side of the interface body, wherein the positive-pressure channel includes a constricted portion configured to provide a pressure drop;

a reduced-pressure channel adapted to deliver the reduced pressure to the dressing, the reduced-pressure channel fluidly coupled between the positive-pressure channel and the second side of the interface body, wherein the reduced pressure substantially corresponds to the pressure drop, and wherein the reduced-pressure channel is fluidly coupled to the positive-pressure channel at the constricted portion; and a pressure-sensing channel in fluid communication between the pressure-sensing port and the second side of the interface body.

24. An interface for providing a reduced pressure to a dressing, the interface comprising:

an interface body having a first side and a second side, the second side adapted to face the dressing;

a positive-pressure channel adapted to deliver positive pressure and extending through the interface body to a positive-pressure outlet proximate the first side of the interface body, the positive-pressure channel including a constricted portion configured to provide a pressure drop; and a reduced-pressure channel fluidly coupled to the positive-pressure channel at or downstream of the constricted portion and between the positive-pressure channel and the second side of the interface body.

* * * * *